United States Patent
Winz et al.

(10) Patent No.: US 10,663,700 B2
(45) Date of Patent: May 26, 2020

(54) ACHROMATIC ASTIGMATIC ANAMORPHIC OBJECTIVE

(71) Applicant: Coherent, Inc., Santa Clara, CA (US)

(72) Inventors: Michele Wayne Winz, Wilsonville, OR (US); Lei Meng, Wilsonville, OR (US)

(73) Assignee: Coherent, Inc., Santa Clara, CA (US)

( * ) Notice: Subject to any disclaimer, the term of this patent is extended or adjusted under 35 U.S.C. 154(b) by 138 days.

(21) Appl. No.: 15/883,542

(22) Filed: Jan. 30, 2018

(65) Prior Publication Data
US 2019/0235216 A1    Aug. 1, 2019

(51) Int. Cl.
| | | |
|---|---|---|
| G02B 13/08 | (2006.01) | |
| G02B 27/14 | (2006.01) | |
| G02B 13/14 | (2006.01) | |
| G02B 27/18 | (2006.01) | |
| G02B 23/04 | (2006.01) | |

(Continued)

(52) U.S. Cl.
CPC ......... *G02B 13/08* (2013.01); *G01N 15/1434* (2013.01); *G01N 15/1459* (2013.01); *G02B 9/16* (2013.01); *G02B 13/146* (2013.01); *G02B 23/04* (2013.01); *G02B 27/0905* (2013.01); *G02B 27/0911* (2013.01); *G02B 27/0966* (2013.01); *G02B 27/1006* (2013.01); *G02B 27/141* (2013.01); *G02B 27/145* (2013.01); *G02B 27/18* (2013.01); *A61B 5/0071* (2013.01); *A61B 5/0075* (2013.01); *G01N 2015/1006* (2013.01); *G01N 2015/1452* (2013.01)

(58) Field of Classification Search
CPC ........ G02B 13/08; G02B 13/10; G02B 13/12; G02B 27/09; G02B 27/0911; G02B 27/0966

USPC .......................................... 359/668–671, 710
See application file for complete search history.

(56) References Cited

U.S. PATENT DOCUMENTS 4,203,652 A * 5/1980 Hanada ................ G02B 6/4206
                                                    359/641
4,253,735 A * 3/1981 Kawamura ............ G02B 27/09
                                                    359/205.1

(Continued)

FOREIGN PATENT DOCUMENTS

| DE | 102013225310 B3 | 5/2015 |
|---|---|---|
| EP | 1403632 A1 | 3/2004 |

(Continued)

OTHER PUBLICATIONS

International Search Report and Written Opinion received for PCT Patent Application No. PCT/US2019/013320, dated Apr. 3, 2019, 12 pages.

(Continued)

*Primary Examiner* — Nicholas R. Pasko
(74) *Attorney, Agent, or Firm* — Morrison & Foerster LLP

(57) ABSTRACT

An anamorphic three-element objective lens projects a plurality of beams of different wavelengths and different diameters into an elongated focal spot in a working-plane. In one transverse direction of the lens, the beams are tightly focused with equal beam-waist widths in the working-plane, defining a height of the focal spot. In another transverse direction, the different beams are focused progressively beyond the working-plane such that the beams have a common beam-width in the working-plane, thereby defining a width of the focal spot.

24 Claims, 4 Drawing Sheets

(51) Int. Cl.
  *G02B 27/10* (2006.01)
  *G02B 9/16* (2006.01)
  *G02B 27/09* (2006.01)
  *G01N 15/14* (2006.01)
  *A61B 5/00* (2006.01)
  *G01N 15/10* (2006.01)

(56) References Cited

U.S. PATENT DOCUMENTS

| | | | | |
|---|---|---|---|---|
| 4,318,594 A * | 3/1982 | Hanada | ............ | G02B 13/10 |
| | | | | 359/641 |
| 4,963,900 A | 10/1990 | Budd et al. | | |
| 5,471,236 A * | 11/1995 | Ito | ............ | B41J 2/473 |
| | | | | 347/233 |
| 6,301,059 B1 * | 10/2001 | Huang | ............ | G02B 27/0025 |
| | | | | 359/668 |
| 6,331,692 B1 * | 12/2001 | Krause | ............ | B23K 26/04 |
| | | | | 219/121.67 |
| 7,538,879 B2 * | 5/2009 | Power | ............ | G01N 21/8422 |
| | | | | 356/432 |
| 7,787,197 B2 * | 8/2010 | Chen | ............ | G01N 15/1434 |
| | | | | 356/338 |
| 10,338,354 B2 * | 7/2019 | Meng | ............ | G02B 27/0911 |
| 2009/0257118 A1 * | 10/2009 | Heritier | ............ | G02B 27/0983 |
| | | | | 359/399 |
| 2015/0355469 A1 * | 12/2015 | Oguri | ............ | G02B 27/0911 |
| | | | | 359/223.1 |
| 2018/0017769 A1 | 1/2018 | Meng et al. | | |

FOREIGN PATENT DOCUMENTS

| | | |
|---|---|---|
| JP | 60-229007 A | 11/1985 |
| WO | 2001/078633 A2 | 10/2001 |
| WO | 2001/078633 A3 | 7/2002 |
| WO | 2011/109763 A2 | 9/2011 |
| WO | 2011/109763 A3 | 3/2012 |

OTHER PUBLICATIONS

International Search Report and Written Opinion received for PCT Patent Application No. PCT/US2017/042007, dated Dec. 1, 2017, 17 pages.

Invitation to Pay Additional Fees received for PCT Patent Application No. PCT/US2017/042007, dated Sep. 29, 2017, 5 pages.

\* cited by examiner

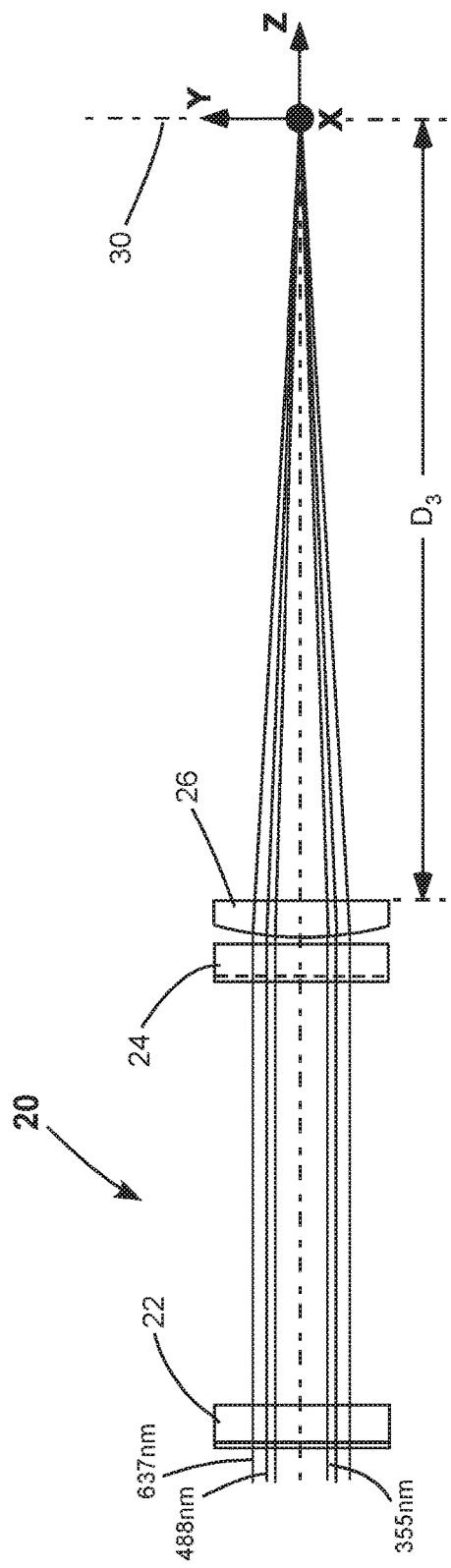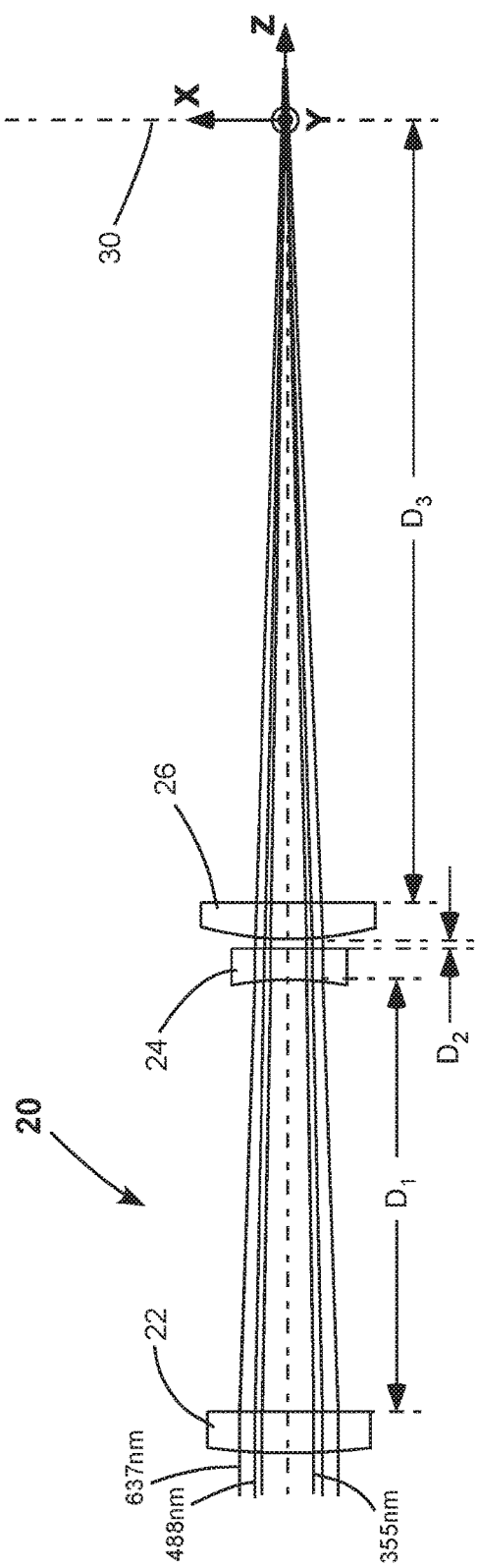

ACHROMATIC ASTIGMATIC ANAMORPHIC OBJECTIVE

TECHNICAL FIELD OF THE INVENTION

The present invention relates in general to projection lenses. The invention relates in particular to anamorphic projection lenses for focusing two or more laser-beams having different wavelengths into a common elliptical focal-spot.

DISCUSSION OF BACKGROUND ART

A basic principle of flow cytometry is the passage of particles in a fluid-stream through a focused beam of laser-radiation. The particles, particularly biological cells, can be detected, identified, counted, and sorted. Cell components are fluorescently labelled and then illuminated by the laser-radiation. Scattered and emitted radiation can be measured to determine the quantity and types of cells present in a sample.

Several detectors are carefully placed around the point where the fluid-stream passes through the focused laser-beam. The suspended particles, which may range in size from 0.2 micrometers (μm) to 150 μm, pass through the focused laser-beam and scatter the laser-radiation. The fluorescently-labelled cell components are also excited by the focused laser-beam and emit radiation (fluorescence) at a longer wavelength than that of the laser-beam. This combination of scattered and fluorescent radiation is measured by the detectors. Measurement data is then analyzed, using special software, by a computer that is attached to the flow cytometer. Thousands of particles per second can be measured and analyzed.

It is generally accepted that the above described flow cytometry process is more flexible and more accurate when more wavelengths of laser-radiation are included in the laser-beam. In practice, this is accomplished by combining component laser-beams from different lasers along a common path to provide a combined laser-beam that is focused into the fluid-stream. Diode-laser modules are typically used for providing the component laser-beams. Commercially available diode-laser modules can provide laser-radiation at fundamental wavelengths ranging from the near ultraviolet to the near infrared.

An increasing number and range of wavelengths presents significant problems in the design and construction of an optical objective for focusing the combined laser-beam into the fluid-stream. It is generally accepted that for focusing two significantly different wavelengths (for example, red and blue) at a common location (focal plane) a focusing objective must include at least two optical-elements having different spectral dispersion. For example, two lenses made of different materials having high and low spectral dispersion. An objective arranged to focus two different wavelengths in a common focal plane is generally referred to as an "achromatic objective".

If three significantly different wavelengths (for example, red, green, and blue) are to be focused at a common location, a focusing objective must include at least three optical-elements having different spectral dispersion. An objective arranged to focus three significantly different wavelengths in a common focal plane is generally referred to as an "apochromatic objective".

In achromatic or apochromatic objectives, individual optical-elements (singlets) of different spectral dispersion may need to be "cemented" together in forms referred to by practitioners of the lens design art as "doublets" or "triplets". These forms can be problematic when ultraviolet wavelengths are included in a flow cytometer, as optical cements (adhesives) may be degraded by ultraviolet laser-radiation.

Based on conventional optical design wisdom, it is expected that the objective required to focus the laser-beam into the fluid-stream will become even more complex and more expensive as additional wavelengths of laser-radiation are included in a flow cytometer. For example, a flow cytometer having four or more wavelengths. This could result in the complexity and cost of a focusing objective imposing a practical upper limit to the number of wavelengths of laser-radiation that can be used in a flow cytometer.

There is need for a simple focusing objective, capable of focusing four or more laser-radiation wavelengths in a common focal plane, but wherein the number of different optical materials (glasses) required is less than the number of different wavelengths to be focused in the common focal plane. Preferably, the focusing objective should not include any cemented doublet or triplet elements. Preferably, the focusing objective will create a combined laser-beam in the common focal plane that is insensitive to any fluctuations of beam-parameters of the component laser-beams from different lasers.

SUMMARY OF THE INVENTION

In one aspect, optical apparatus in accordance with the present invention comprises an illumination source arranged to deliver a plurality of collimated coaxial laser-beams. Each laser-beam has a different wavelength and a different beam-width. An anamorphic objective is provided that has first and second transverse directions orthogonal to each other. The objective is arranged to receive the laser-beams from the illumination source and to project the laser-beams towards a working-plane at a working-distance from the objective. The objective is configured and arranged such that, in the first transverse direction of the objective, the laser-beams are each focused to a beam-waist located about in the working-plane and having about the same beam-waist width. In the second transverse direction of the objective, the laser-beams are focused to beam-waists at different locations that are displaced from the working-plane. The displacements are selected such that the laser-beams have about the same beam-width in the working-plane.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain principles of the present invention.

FIG. 2A and FIG. 2B are respectively a side-view and a plan-view of a preferred arrangement of the anamorphic objective of FIG. 1, including two cylindrical lens-elements and a rotationally-symmetric lens-element.

DETAILED DESCRIPTION OF THE INVENTION

Figure 1:
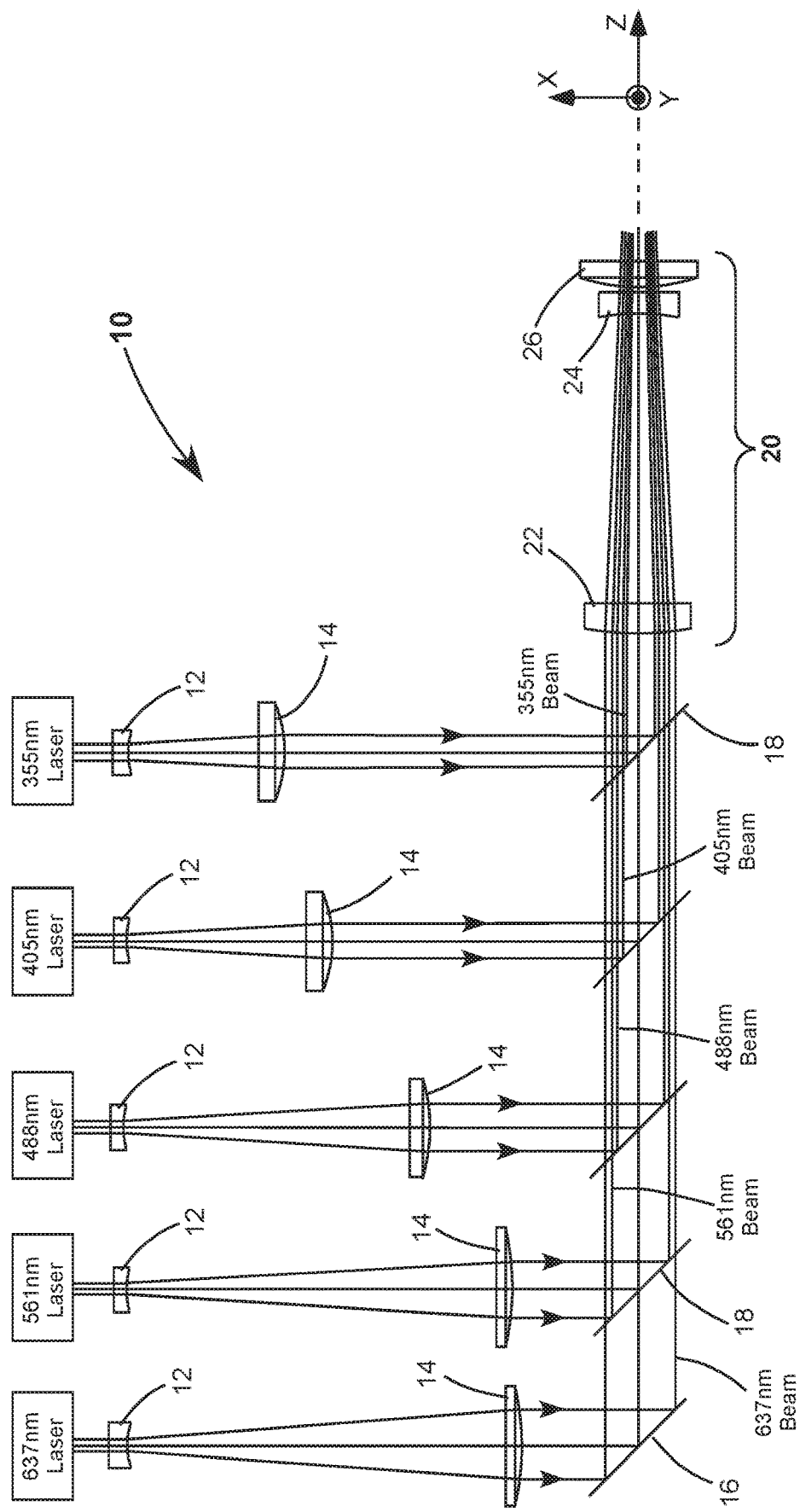
FIG. 1 is a plan-view schematically illustrating a preferred embodiment of optical apparatus in accordance with the present invention, including a plurality lasers delivering beams of radiation having a corresponding plurality of different wavelengths, a corresponding plurality of telescopes arranged to collimate and expand the respective beams to different diameters that are about proportional to the different wavelengths, a beam-combiner for coaxially combining the collimated and expanded beams, and an anamorphic focusing objective arranged to focus the beams in a working-plane of the apparatus.

Turning now to the drawings, wherein like features are designated by like reference numerals, FIG. 1 is a plan-view schematically illustrating a preferred embodiment 10 of optical apparatus in accordance with the present invention. Optical apparatus 10 includes a plurality (here 5) of lasers, explicitly indicated in the drawing according to the wavelength of the laser-beam generated by each laser. The wavelengths are 355 nanometers (nm), 405 nm, 488 nm, 561 nm, and 637 nm. These wavelengths are exemplary and should not be considered limiting, but are consistent with wavelengths of commercially available diode-lasers and diode-pumped solid-state lasers. Associated with the lasers is a corresponding plurality of telescopes (beam expanders), each thereof formed by a negative lens 12 and a positive lens 14. The lenses in the different laser beams are designated by the same reference numeral for similarity of function, but may have different specifications, consistent with different degrees of beam-expansion. Exemplary specifications are discussed further hereinbelow. Laser-beams delivered by the telescopes are collimated and circular in cross-section.

It is understood that the term "collimated", as used in this description and the appended claims, recognizes that laser-beams are rarely precisely collimated, even when precise collimation is intended. The degree of collimation varies with distance from a collimating device due to Gaussian beam propagation effects, as is well known in the art. It is also understood that the term "circular" allows that the laser-beams may be slightly elliptical in cross-section, having major and minor axis that are the same to within a few percent, rather than being precisely circular. Herein below, the orientation and arrangement of elements and beams in optical apparatus 10 will be discussed with reference to Cartesian X-, Y-, and Z-axes, which are depicted on the drawing.

The beam-diameters of individual laser-beams decrease in about proportion to wavelength, and are combined coaxially along the Z-axis by a turning mirror 16 and four dichroic beam-combining mirrors 18. Herein, "beam-diameter" is used when beams are about circular in cross-section and "beam-width" is used when beams are non-circular (elliptical) in cross-section. Like telescope lenses 12 and 14, beam-combining mirrors 18 are designated by the same reference numeral for similarity of function, but have different specifications dependent on the particular wavelengths being transmitted or reflected. Dichroic beam-combining arrangements are well known to practitioners of the art and a detailed description thereof is not necessary for understanding principles of the present invention. The lasers, the telescopes, the turning mirror, and the beam-combining mirrors collectively form an illumination source delivering a plurality of collimated coaxial laser-beams, having different beam-widths that depend on wavelength.

The coaxially combined laser-beams are delivered to an inventive three-element anamorphic focusing objective 20. Anamorphic objective 20 includes two cylindrical lenses 22 and 24, and a rotationally-symmetric lens 26. The Z-axis is a common optical axis for lenses 22, 24, and 26, as well as the propagation axis of the coaxially combined laser-beams. The anamorphic objective projects the laser-beams along the Z-axis towards a working-plane (not depicted), to form an elongated focal spot in the working-plane. A detailed description of functions of anamorphic objective 20 is presented further hereinbelow.

Exemplary specifications for telescope lenses 12 and 14 in optical apparatus 10 are presented in TABLE 1 below. "EFL" is effective focal length, "Incident Beam-Diameter" is the beam-diameter of the laser-beam incident on telescope lens 12, and "Spacing" is the distance between telescope lenses 12 and 14. EFL, Incident Beam Diameter, and Spacing all have units of millimeters (mm).

TABLE 1

| Laser Wavelength | Incident Beam-Diameter | 12 EFL | Spacing | 14 EFL |
|---|---|---|---|---|
| 355 nm | 1 | −12 | 9.8 | 24.3 |
| 405 nm | 1 | −12 | 13.7 | 28.1 |
| 488 nm | 1 | −12 | 20.5 | 34.8 |
| 561 nm | 1 | −12 | 26.7 | 40.8 |
| 637 nm | 1 | −12 | 33.5 | 47.8 |

The specifications of TABLE 1 will provide nominal beam-diameters for the 355 nm, 405 nm, 488 nm, 561 nm and 637 nm wavelengths of about 2.0 mm, about 2.3 mm, about 2.9 mm, about 3.4 mm, and about 4.0 mm, respectively. The nominal beam-diameters are approximately proportional to the wavelengths of the laser-beams.

FIG. 2A and FIG. 2B schematically illustrate details a preferred embodiment of anamorphic objective 20 of FIG. 1. Only three of the five coaxially-combined laser-beams are depicted for simplicity of illustration. In this example, the laser-beams are all depicted having circular cross-sections when incident on anamorphic objective 20. However, the collimated laser-beams delivered by the telescopes could be non-circular in cross-section, without departing from the spirit and scope of the present invention.

FIG. 2A is a side-view in the Y-Z plane of the anamorphic objective. In this view, the incident laser-beams are tightly focused by anamorphic objective 20 in a working-plane 30, at a working-distance $D_3$ from the rotationally-symmetric lens 26. In the Y-Z plane, all the beam-waists are located about in working-plane 30 and all the beam-waist widths are the same. This common beam-waist width defines the height of the above-discussed elongated focal spot in the working-plane. By way of example, if working-plane 30 contains a particle stream being illuminated in a flow cytometer, the flow direction of the particle stream would be along the Y-axis.

FIG. 2B is a plan-view in the X-Z plane of the anamorphic objective. Cylindrical lenses 22 and 24 are axially separated by a distance $D_1$. Negative cylindrical lens 24 is axially separated by a distance $D_2$ from rotationally-symmetric lens 26. Positive cylindrical lens 22 and negative cylindrical lens 24 have optical power in the X transverse direction only and no optical power in the Y transverse direction. Rotationally-symmetric lens 26 has positive optical power in both the X and Y transverse directions. In this example, cylindrical lens 22 is a plano-convex optical-element, cylindrical lens 24 is a plano-concave optical-element, and rotationally-symmetric lens 26 is a plano-convex optical-element. In the above mentioned flow cytometer arrangement, the particle stream flowing along the Y-axis would be perpendicular to the plane of the drawing.

In the X-Z plane, the laser-beams are focused at different distances beyond working-plane, depending on wavelength. The distances are selected such that all of the laser-beams have about the same beam-width in working-plane 30. This common beam-width defines the width of the above-discussed elongated focal spot. In principle, inventive anamorphic objective 20 is made intentionally and significantly astigmatic to achieve this common beam-width for all laser-beams. A detailed description of this intentionally introduced and significant astigmatism is set forth below with reference to FIG. 3.

Figure 3:
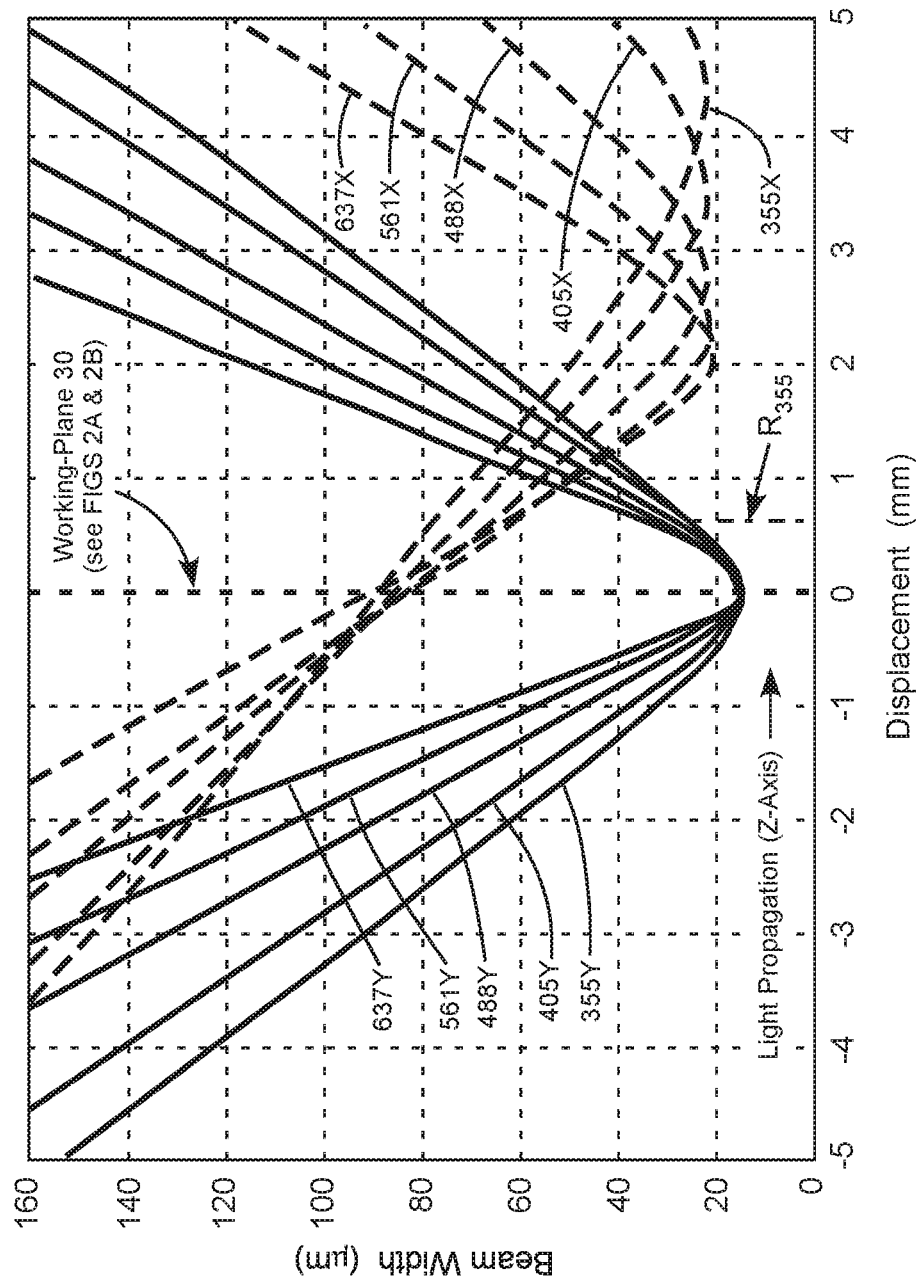
FIG. 3 is a graph schematically illustrating beam-width as a function of displacement from the working-plane in one example of the lens of FIGS. 2A and 2B, with beam-waists of all beams in a Y transverse direction located in the working-plane and having the same beam-waist width, and beam-waists in a X transverse direction located beyond the working-plane at different wavelength-dependent distances selected such that the beams have a common beam-width in the working-plane.

FIG. 3 is a graph schematically illustrating computed beam-width as a function of displacement along the Z-axis from working-plane 30 of FIG. 2. The graph was generated using ZEMAX optical design software, available from Zemax LLC, of Kirkland, Wash.

It is assumed that the beam-diameters of the laser-beams incident on anamorphic objective 20 are 2.0 mm, 2.3 mm, 2.9 mm, 3.4 mm, and 4.0 mm for respectively the 355 nm, 405 nm, 488 nm, 561 nm, and 637 nm wavelengths. It is assumed that positive cylindrical lens 22 has an EFL of 131.3 mm, a center thickness of 3.6 mm, and a radius of curvature (ROC) of 60.19 mm. Negative cylindrical lens 24 has an EFL of −87.5 mm, a center thickness of 2.9 mm, and a ROC of 40.13 mm. The ratio of the absolute EFLs of cylindrical lenses 22 and 24 is about 1.5. Rotationally-symmetric lens 26 has an EFL of 70 mm, a center thickness of 2.9 mm, and a ROC of 32.2 mm. Distances $D_1$, $D_2$, and $D_3$ of FIGS. 2A and 2B are assumed to be 36.71 mm, 2.5 mm, and 67.5 mm, respectively. All the lenses are made from fused silica, which is particularly advantageous for transmitting ultraviolet radiation, such as the 355 nm radiation in the present example.

Working-plane 30 in FIG. 3 is at displacement zero (0 mm). Beam-waists of all the laser-beams in the transverse Y transverse direction (solid curves) are located in the working-plane. The laser-beams are designated by wavelength and transverse direction, for example "637Y" for 637 nm in the Y transverse direction. The beam-diameters of the laser-beams incident on anamorphic objective 20 are selected such that all the laser-beams have the same beam-waist width in the Y transverse direction, here, about 15 µm.

Beam-waists in a X transverse direction (dashed curves) are located at different displacements, selected such that the laser-beams have a common beam-width in working-plane 30 in the X transverse direction, here, about 90 µm. This arrangement creates an elongated focal spot having height× width dimensions of about 15 µm×about 90 µm in the working-plane. Here, again, the beam-waists are designated by wavelength and transverse direction, for example "355X".

It can be seen that the beam-waist width for all laser-beams in the X transverse direction is about 21 µm, but theses beam-waists are spread along the Z-axis, over a distance of about 2.5 mm between the closest and furthest from the working-plane. The closest beam-waist (637X) is displaced from the working-plane by more than 2.0 mm. This is significantly greater (about four-times greater) than one Rayleigh range of the 355 nm laser-beam in the Y transverse direction, labelled "$R_{355}$" in the drawing. The shortest wavelength 355 nm laser-beam has the broadest Rayleigh range. "Rayleigh range" is the distance from a beam-waist to a transverse plane where the beam-width is equal to √2 times the corresponding beam-waist width. It can also be seen that the spread of all beam-waists in the X transverse direction is significantly greater than the Rayleigh range of any one of them.

While the above described example of the inventive anamorphic objective relies on locating the beam-waists in the X transverse direction beyond the working-plane to achieve a common beam-size in the working-plane, a similar result can be achieved if the beam waists are located closer than the working-plane. This is schematically depicted in the graph of FIG. 4.

Figure 4:
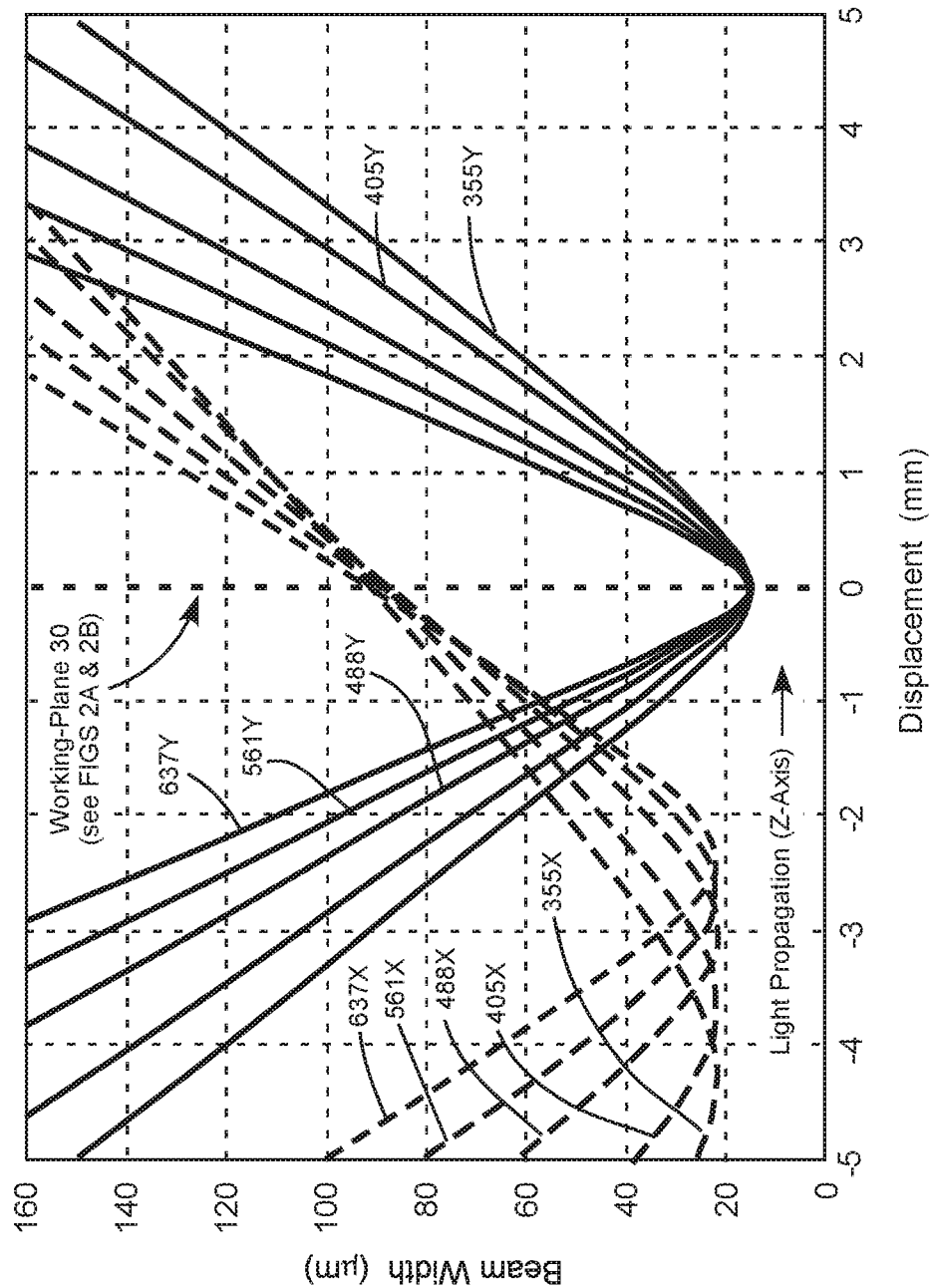
FIG. 4 is a graph schematically illustrating beam-width as a function of displacement from the working-plane in another example of the lens of FIGS. 2A and 2B, with beam-waists of all beams in a Y transverse direction located in the working-plane and having the same beam-waist width, and beam-waists in a X transverse direction located closer than the working-plane at different wavelength-dependent distances selected such that the beams have a common beam-width in the working-plane.

In the example of FIG. 4, the basic lens configuration is as depicted in FIG. 2A and 2B. It is assumed that the beam-diameters the laser-beams incident on anamorphic objective 20 are 2.0 mm, 2.3 mm, 2.9 mm, 3.4 mm, and 4.0 mm for respectively the 355 nm, 405 nm, 488 nm, 561 nm, and 637 nm wavelengths. It is assumed that positive cylindrical lens 22 has an EFL of 33.3 mm, a center thickness of 3.6 mm, and a ROC of 15.3 mm. Negative cylindrical lens 24 has an EFL of −22.2 mm, a center thickness of 2.9 mm, and a ROC of 10.2 mm. Here, again, the ratio of the absolute EFLs of cylindrical lenses 22 and 24 is about 1.5. Rotationally-symmetric lens 26 has an EFL of 70 mm, a center thickness of 2.9 mm, and a ROC of 32.2 mm. Distances $D_1$, $D_2$, and $D_3$ of FIGS. 2A and 2B are assumed to be 8.5 mm, 2.5 mm, and 67.6 mm respectively. All lenses are made from fused silica.

In some applications it is advantageous to configure the individual elongated focal spots into a linear array of focal spots in the Y transverse direction, rather than combining them into a single elongated focal spot, to form a stacked arrangement of elongated focal spots in the working plane having different wavelengths. Those skilled in the art of optical design would recognize that such an arrangement can be achieved using the inventive anamorphic objective, without departing from the spirit and scope of the present invention. For example, in a configuration having slightly different angles-of-incidence of the collimated beams delivered to the anamorphic objective. Angle-of-incidence can be slightly adjusted by tilting the corresponding turning mirror or beam-combining mirror. The combined laser-beams would be still be almost, but not precisely, coaxial.

Elongated focal spots having dimensions other than 15 µm×90 µm can be formed by replacing the anamorphic objective optics. For example, elongated focal spots having dimensions 10 µm×60 µm or 10 µm×70 µm. From the description provided herein, those skilled in the art would recognize that elongated focal spots having a broad range of height: width ratios can be formed; over at least a range from 1:2 to 1:20. In general, assuming laser-beams having about the same beam-quality ($M^2$ as is known in the art), the rotationally-symmetric lens is selected for the required working-distance. The beam-widths of the collimated laser-beams are set by adjusting the corresponding telescopes to achieve the required beam-waist width in the Y transverse axis. The cylindrical lenses are selected to achieve the required beam-width in the X transverse axis, preferably maintaining the about 1.5 ratio of the absolute EFLs of the cylindrical lenses, discussed above.

An advantage of the present invention is that the height-to-width ratio of the elongated focal spot can be modified without replacing the anamorphic objective or any of its lenses by simply adjusting working-distance $D_3$ and the axial locations of the telescope lenses. To modify just the width of the elongated focal spot, the working-distance is adjusted to achieve the desired width in the X transverse direction, then the axial locations of the telescope optics are adjusted to refocus the laser-beams to the working-plane in the Y transverse direction.

Another advantage of the present invention is that the transverse location of each individual elongated focal spot in the working-plane is relatively insensitive to fluctuations in beam-pointing of the corresponding laser. For the exemplary elongated focal spot having dimensions 15 μm×90 μm, substantial 100 micro-radian changes in beam-pointing would cause only a 10 μm displacement along the X transverse axis or a 7 μm displacement along the Y transverse axis. The about 1.5 ratio of the absolute EFLs of cylindrical lenses 22 and 24 was found to be favorable for minimizing sensitivity to fluctuations in beam-pointing.

In summary, the challenge of designing and fabricating an achromatic anamorphic objective for projecting multiple beams having different wavelengths is mitigated in the present invention by eliminating the need to make the objective stigmatic, allowing astigmatism to be used as a design tool. Those skilled in the art of optical design are will recognize that the "significant astigmatism" depicted in FIG. 3 and FIG. 4, which is key to the function of the inventive anamorphic objective, must be deliberately introduced into the design of the anamorphic objective to achieve the described result. The magnitude of the astigmatism is far greater than any residual astigmatism that may be present in a lens designed to be stigmatic.

The present invention is described above with reference to preferred embodiments. The invention, however, is not limited to the embodiments described and depicted herein. Rather the invention is limited only by the claims appended hereto.

What is claimed is:

1. Optical apparatus, comprising:
an illumination source arranged to deliver a plurality of collimated laser-beams, each laser-beam thereof having a different wavelength and a different beam-width;
an anamorphic objective having first and second transverse directions orthogonal to each other, the objective arranged to receive the laser-beams from the illumination source and to project the laser-beams along a propagation direction towards a working-plane at a working-distance from the objective; and
wherein the objective is configured and arranged such that, in the first transverse direction of the objective, the laser-beams are each focused to a beam-waist located about in the working-plane and having about the same first beam-waist width, and in the second transverse direction of the objective, the laser-beams are focused to beam-waists at different locations along the propagation direction, said different locations being displaced from the working-plane and from each other, the displacements selected such that the laser-beams have about the same second beam-width in the working-plane, the second beam-width being larger than the first beam width.

2. The apparatus as recited in claim 1, wherein in the second transverse direction, the laser-beams are focused further from the illumination source than the working-plane.

3. The apparatus as recited in claim 1, wherein in the second transverse direction, the laser-beams are focused closer to the illumination source than the working-plane.

4. The apparatus as recited in claim 1, wherein in the working-plane, the beam-width of the laser-beams in the first transverse direction is about 15 μm and the beam-width of the laser-beams in the second transverse direction is about 90 μm.

5. The apparatus as recited in claim 1, wherein in the working-plane, the beam-width of the laser-beams in the first transverse direction is about 10 μm and the beam-width of the laser-beams in the second transverse direction is about 70 μm.

6. The apparatus as recited in claim 1, wherein the collimated beams from the illumination source have a circular cross-section.

7. The apparatus as recited in claim 1, wherein the laser-beams form an elongated focal spot in the working-plane, the about same first beam-waist width in the first transverse direction defining a height of the focal spot, and the about same second beam-width in the second transverse direction defining a width of the focal spot.

8. The apparatus as recited in claim 1, wherein the laser-beams form a stacked arrangement of elongated focal spots in the working-plane, in the first transverse direction, each focal spot having a different wavelength.

9. The apparatus as recited in claim 1, wherein the plurality of collimated laser-beams are coaxial.

10. The apparatus as recited in claim 1, wherein in the second transverse direction, the beam-waists are displaced from the working-plane by more than one Rayleigh-range of the focused laser-beams in the first transverse direction.

11. The apparatus as recited in claim 10, wherein the different beam-waists in the second transverse direction are displaced from the working-plane by at least four-times the Rayleigh range of the focused laser-beams in the first transverse direction.

12. The apparatus as recited in claim 1, wherein the anamorphic objective consists of first, second, and third lens-elements spaced-apart from each other along a common optical axis, the first lens-element having zero optical power in the first transverse direction and positive optical power in the second transverse direction, the second lens-element having zero optical power in the first transverse direction and negative optical power in the second transverse direction, and the third lens-element having positive optical power in both the first and second transverse directions.

13. The apparatus as recited in claim 12, wherein the absolute effective focal-length of the second lens-element is 1.5 times the absolute effective focal-length of the first lens-element.

14. The apparatus as recited in claim 12, wherein the first, second, and third lens-elements are singlet lens-elements.

15. The apparatus as recited in claim 14, wherein the first, second, and third lens-elements are made from the same optical material.

16. The apparatus as recited in claim 15, wherein the optical material is fused silica.

17. Optical apparatus, comprising:
an illumination source arranged to deliver a plurality of collimated laser-beams, each laser-beam thereof having a different wavelength and a different beam-width;
an anamorphic objective having first and second transverse directions orthogonal to each other, the objective arranged to receive the laser-beams from the illumination source and to project the laser-beams along a propagation direction towards a working-plane at a working-distance from the objective;

wherein the anamorphic objective consists of first, second, and third lens-elements arranged in numerical order along a propagation axis, the first lens-element having zero optical power in the first transverse direction and positive optical power in the second transverse direction, the second lens-element having zero optical power in the first transverse direction and negative optical power in the second transverse direction, and the third lens-element having positive optical power in both the first and second transverse directions; and wherein the first, second, and third lens-elements are arranged such that, in the first transverse direction of the objective, the laser-beams are each focused to a beam-waist located about in the working-plane and having about the same first beam-waist width, and in the second transverse direction of the objective, the laser-beams are focused to beam-waists at different locations along the propagation direction, said different locations being displaced from the working-plane and from each other, the displacements selected such that the laser-beams have about the same second beam-width in the working-plane, the second beam-width being larger than the first beam width.

18. The apparatus as recited in claim 17, wherein the plurality of collimated laser-beams are coaxial.

19. The apparatus as recited in claim 17, wherein the laser-beams form an elongated focal spot in the working-plane, the about same first beam-waist width in the first transverse direction defining a height of the focal spot, and the about same second beam-width in the second transverse direction defining a width of the focal spot.

20. The apparatus as recited in claim 17, wherein the laser-beams form a stacked arrangement of elongated focal spots in the working-plane, in the first transverse direction, each focal spot having a different wavelength.

21. The apparatus as recited in claim 17, wherein in the second transverse direction, the beam-waists are displaced from the working-plane by more than one Rayleigh-range of the focused laser-beams in the first transverse direction.

22. The apparatus as recited in claim 21, wherein the different beam-waists in the second transverse direction are displaced from the working-plane by at least four-times the Rayleigh range of the focused laser-beams in the first transverse direction.

23. The apparatus as recited in claim 17, wherein the first, second, and third lens-elements are singlet lens-elements.

24. The apparatus as recited in claim 23, wherein the first, second, and third lens-elements are made from the same optical material.

* * * * *